(12) United States Patent
Klett-Loch

(10) Patent No.: US 9,850,274 B2
(45) Date of Patent: Dec. 26, 2017

(54) PEPTIDE COMBINATION

(75) Inventor: Guenther Klett-Loch, Dielsdorf (CH)

(73) Assignee: GKL-Biotec AG, Dielsdorf (CH)

( * ) Notice: Subject to any disclaimer, the term of this patent is extended or adjusted under 35 U.S.C. 154(b) by 632 days.

(21) Appl. No.: 13/142,931

(22) PCT Filed: Dec. 30, 2009

(86) PCT No.: PCT/DE2009/001819
§ 371 (c)(1),
(2), (4) Date: Sep. 23, 2011

(87) PCT Pub. No.: WO2010/075849
PCT Pub. Date: Jul. 8, 2010

(65) Prior Publication Data
US 2012/0010149 A1    Jan. 12, 2012

(30) Foreign Application Priority Data
Dec. 30, 2008    (DE) .......... 10 2008 063 256

(51) Int. Cl.
*A61K 38/00* (2006.01)
*C07K 1/04* (2006.01)
*C08G 69/10* (2006.01)

(52) U.S. Cl.
CPC .............. *C07K 1/047* (2013.01); *C08G 69/10* (2013.01); *Y02P 20/55* (2015.11)

(58) Field of Classification Search
None
See application file for complete search history.

(56) References Cited

U.S. PATENT DOCUMENTS

| | | | |
|---|---|---|---|
| 6,458,761 B2 | 10/2002 | Klett-Loch | |
| 6,803,186 B2 * | 10/2004 | Davenport et al. | 435/4 |
| 2005/0107303 A1 * | 5/2005 | Butterwick et al. | 514/17 |
| 2005/0250850 A1 * | 11/2005 | Murakami et al. | 514/561 |
| 2006/0088516 A1 | 4/2006 | Klett-Loch | |
| 2007/0299015 A1 * | 12/2007 | Harris et al. | 514/18 |

FOREIGN PATENT DOCUMENTS

| | | | |
|---|---|---|---|
| DE | 103 27 518 A1 | | 1/2005 |
| EP | 0 983 080 A1 | | 3/2000 |
| WO | WO2007079977 | * | 7/2007 |
| WO | WO 2008/028951 | * | 3/2008 |

OTHER PUBLICATIONS

Itazaki et al, Isolation and structural elucidation of new cyclotetrapeptides, trapoxins A and B, having detransformation activities as antitumor agents, The Journal of Antibiotics, Dec. 1990 1524-1532.*
Ramm et al, Studies of the biosynthesis of tentoxin by Alternaria alternata, Microbiology (1994), 140, 3257-3266.*
Yang et al, Structure—activity relationships of naturally occurring and synthetic opioid tetrapeptides acting on locus coeruleus neurons, European Journal of Pharmacology 372_1999. 229-236.*
International Preliminary Report on Patentability for Int. App. No. PCT/DE2009/001819, Jul. 5, 2011, GKL-Biotec AG.
Written Opinion of the International Searching Authority for Int. App. No. PCT/DE2009/001819, Jun. 30, 2011, GKL-Biotec AG.
Ostresh, J., et al., "Peptide Libraries: Determination of Relative Reaction Rates of Protected Amino Acids in Competitive Couplings," *Biopolymers*, 1994, vol. 34(12), pp. 1681-1689.
Birr et al., "Statistic Combination of Thymus Peptides, a Synthetic Library Mimicing the Physiological Environment," Peptides, pp. 62-63, (1998).
Birr, "The GMP-based drug substance SCTL development aiming at prevention of opportunistic infections after x-ray- and chemotherapy of cancer. A synthetic combinatorial tetrapeptide library substitution for calf thymus extract," Biotechnologia ACTA, 6(4):162-171, (2013).
Boutin et al., "Investigation of S-Farnesyl Transferase Substrate Specificity with Combinatorial Tetrapeptide Libraries," Cellular Signalling, 11(1):59-69, doi: 10.1016/S0898-6568(98)00032-1, (1999).
CA Application No. 2,753,224, Office Action, dated May 19, 2016.
Dooley et al., "Selective Ligands for the μ, δ, and κ☐ Opioid Receptors Identified from a Single Mixture Based Tetrapeptide Positional Scanning Combinatorial Library," The Journal of Biological Chemistry, 273(30):18848-18856, (1998).
EPO Application No. 09808930.3, Examination Report, dated Feb. 10, 2014, machine translation of pp. 3-6.
EPO Application No. 09808930.3, Examination Report, dated Dec. 8, 2015, machine translation of pp. 3-6.
Ferry et al., "Selection of a histidine-containing inhibitor of gelatinases through deconvolution of combinatorial tetrapeptide libraries," Molecular Diversity, 2(3):135-146, doi:10.1007/BF01682201, (1997).
Harris et al., "Rapid and general profiling of protease specificity by using combinatorial fluorogenic substrate libraries," PNAS, 97(14):7754-7759, (2000).
Arakawa et al., "Biotechnology applications of amino acids in protein purification and formulations," Amino Acids, 33:587-605, doi: 10.1007/s00726-007-0506-3 (2007).
EPO Application No. 09808930.3, Examination Report, dated Jun. 2, 2017, machine translation of pp. 3-6.

* cited by examiner

*Primary Examiner* — James H Alstrum Acevedo
*Assistant Examiner* — Sergio Coffa
(74) *Attorney, Agent, or Firm* — Alston & Bird LLP

(57) ABSTRACT

The invention relates to a peptide combination characterized by peptides each having the same sequence length (SEQL), that can be produced from a mixture (A) comprising a number x of amino acids having a protected acid group or a number z of peptides having an acid group protected by means of a protecting group and an activated amino group, wherein the amino acids are present in the mixture (A) in particular adjustable molar ratios, and a mixture (B) comprising a number y of amino acids having an amino group protected by means of a protecting group, wherein the amino acid molar ratios of the mixture (B) are equal to the amino acid molar ratios of the mixture (A), and wherein the number x=y.

7 Claims, 2 Drawing Sheets

```
                      SEQUENCE LISTING

<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Lys Pro Arg
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gln Pro Arg
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Lys Pro Pro Arg
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Pro Trp Phe
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Pro Phe Phe
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Pro Leu Gly
1
```

PEPTIDE COMBINATION

CROSS-REFERENCE TO RELATED APPLICATIONS

This application is a U.S. National Stage Application based on PCT/DE2009/001819, filed Dec. 30, 2009, which claims the benefit of German Application No. 10 2008 063 256.2, filed on Dec. 30, 2008, all of which are herein incorporated by reference in their entirety.

FIELD OF THE INVENTION

Reference to a Sequence Listing

This application includes a sequence listing submitted herewith as a text filed named "407500_SEQLST.TXT" created on Apr. 25, 2016, and containing 1,415 bytes. The material contained in this text file is incorporated by reference in its entirety for all purposes.

The present invention relates to a peptide combination, a method for the synthesis of peptide combinations, and a peptide library.

BACKGROUND OF THE INVENTION

Synthetic, statistical thymus peptide combinations and the use thereof as preparations with immunological and/or endocrinological efficacy are known from European patent 0 983 080 B1. The preparation containing thymus peptide combinations can be obtained by sequencing chemically suitable, derivatized amino acids into short-chain peptides, wherein the proportion which is characteristic for thymus tissue, and the pattern of the amino acids is formed such that it is possible to achieve a dose-dependent increase in the proliferation of human lymphocytes using the preparation. The starting point for the synthesis of synthetic, statistical thymus peptide combinations is the analysis of individual peptides from partial hydrolysates of thymus proteins. By reacting amino acids in a proportion and pattern which is characteristic of thymus tissue, the peptides known from the partial hydrolysates can be synthesized from synthetic amino acids, which overall form the characteristic synthetic, statistical thymus peptide combination. For this reason, it is possible to rule out a risk of BSE.

A synthetic preparation containing combinations of peptides and a method for the production thereof is also known from German patent application 103 27 518 A1. The invention claimed in this application deals with partial hydrolysates from human tissue, wherein the result of the partial hydrolysis depends on special enzyme combinations. This means that the result can be controlled in a targeted manner by means of the selection of enzymes in special combinations.

SUMMARY OF THE INVENTION

Taking the prior art described above as a starting point, the present invention addresses the problem of providing combinations of peptides in consistently reproducible quality and quantity, wherein said peptide combinations are, by way of example, the basis for a therapeutic procedure.

Moreover, the present invention addresses the problem of providing a method for the synthesis of combinations of peptides, wherein said peptide combinations can be produced by means of the method in a reproducible manner, with respect to the quality and quantity thereof.

Finally, the present invention addresses the problem of providing a peptide library containing peptide combinations which each have the same sequence length, and which have a certain, determined proportion of amino acids.

With respect to the problem of providing combinations of peptides with consistently reproducible quality and quantity, the combination of peptides according to the invention addresses the problem above by means of the features of claim 1. According to said claim, a combination of peptides is characterized by peptides each having the same sequence length (SEQL), wherein the same can be produced from a mixture (A) which contains:

a number x of amino acids having a protected acid group, or a number z of peptides having acid groups protected by means of protecting groups and having activated amino groups, wherein the amino acids are present in the mixture (A) in certain, adjustable mole ratios, and a mixture (B), containing a number y of amino acids having amino groups protected by means of protective groups, wherein the amino acid mole ratios in the mixture (B) are equal to the amino acid mole ratios in the mixture (A), and wherein the number $x=y$.

DETAILED DESCRIPTION OF THE INVENTION

According to the invention, it has been observed that it is possible to provide peptide combinations having peptides of the same sequence length, which can be the basis for a therapeutically effective preparation and which are reproducible in quality and quantity, by means of the mixing of two amino acid mixtures A and B which contain an identical number of amino acids, which can be adjusted in terms of their mole ratios—that is, by means of creating a reaction between two mixtures of amino acids which are identical in their composition except for the protective groups thereof, and/or additionally to create a reaction between synthetic peptides from the mixtures A and B, having acid groups protected by means of protective groups, and having activated amino groups, and the mixture B. With regards to the consistent quality and quantity of the combinations of peptides, the reader is initially directed to FIG. 2, which shows a comparison of 3 peptide combinations (GKL-02) produced independently of each other, in a chromatographic solution (chromatogram). For example, in the preparation produced by the applicant, having the name GKL-02, the mole ratios of the tetrapeptides—that is, the tetrapeptide library consisting of a mixture of 11 amino acids—can be, by way of example, 8.33 mol-% for the amino acid asparaginic acid (Asp), 9.53 mol-% for the amino acid glutamic acid (Glu), 15.18 mol-% for the amino acid proline (Pro), and 37.10 mol-% for glycine (Gly), etc. Both natural and synthetic amino acids, or a combination of natural and synthetic amino acids, can be used for the combination of peptides according to the invention.

The combination of peptides preferably consists of 11 amino acids which can be combined with 11 amino acids which have identical amino acid groups, or further, one peptide produced from 11 and 11 amino acids which have identical amino acid groups can be combined with 11 identical amino acids, etc. This means that the peptides of dipeptides (SEQL=2) can be combined into infinitely ($\infty$) large peptides (SEQL≥2). As such, the smallest peptide combination according to the invention is the dipeptide with $z=(x*y)$—that is, a peptide produced from the mixture A with a number of x amino acids, and the mixture B with a number of y amino acids, consisting of two amino acids, wherein the amino acids of mixture A are protected at their acid groups during synthesis by means of protective groups, and the amino acids of mixture B are protected at their amino groups by means of protective groups, the same being cleaved off following the synthesis to give dipeptides, and the number x is equal to the number y.

In a particularly preferred configuration, tetrapeptides can be produced which consist of four amino acids. Many tetrapeptides are pharmacologically active and often show an affinity and specificity for a number of receptors. Both linear and cyclic tetrapeptides can be contemplated for the preferred tetrapeptides, wherein the cyclic tetrapeptides can be created by a four-way peptide bond or by covalent bonding.

Examples of tetrapeptides are tuftsin (L-threonyl-L-lysyl-L-prolyl-L-arginine) (SEQ ID NO: 1), a tissue hormone related to phagocytosis, rigin (glycyl-L-glutaminyl-L-prolyl-L-arginine) (SEQ ID NO: 2), having similar functions as tuftsin, postin (Lys-Pro-Pro-Arg) (SEQ ID NO: 3), which is the N-terminal tetrapeptide of cystatin C and is an antagonist of tuftsin, endomorphin-1 (H-Tyr-Pro-Trp-Phe-NH2) (SEQ ID NO: 4) and endomorphin-2 (H-Tyr-Pro-Phe-Phe-NH2) (SEQ ID NO: 5), peptamides with the highest affinity and specificity to opioid receptors located in the central and peripheral nervous system, and tyrosin-MIF-1 (Tyr-Pro-Leu-Gly-NH2) (SEQ ID NO: 6), for example, which is an endogenous opioid modulator. In general, combinations of peptides can be used in the areas of oncology, immunology, endocrinology, and dermatology. However, combinations of peptides can also be used in the area of neurology, as described for the endomorphins, and in other clinical areas.

So that the amino acid mixtures A and B can be synthesized together in a particular direction to make a peptide, the side chain functional groups, as described above, must be protected by means of protective groups, and the protective groups must then be removed again. For this purpose, suitably protected amino acid building blocks are used according to the synthesis strategy. The following protective groups for the amino acid functional groups can be used for the synthesis, by way of example: fluorenylmethyloxycarbonyl (FMOC) and tert-butyloxycarbonyl (BOC) for amino groups, benzylester (OBZL) and tert-butylester (OTBU) for acid groups, 2,2,4,6,7-pentamethyldihydrobenzofuran-5-sulfonyl (PBF), (2,2,5,7,8-pentamethyl-chroman-6-sulfo-nyl) (PMC), trityl (TRT), nitro ($NO_2$) as protection for the side chain functional groups. BOC amino acids are preferably reacted with amino acid benzyl esters, hydrochlorides, or -tosylates. Standard coupling reagents, such as N-ethyl-N'-diisopropyl carbodiimide (EDC, HCL), dicyclohexyl carbodiimide (DCC), N,N'-diisopropyl carbodiimide (DIC), or 2-(1-H-benzotriazole-1-yl)-1,1,3,3-tetramethyluronium tetrafluoroborate (TBTU), for example, can be used for the synthesis of the peptides. The peptides are added step by step, then at the end of the synthesis, all protective groups are removed.

The peptide synthesis is preferably carried out in solution; however, a solid-state synthesis can also be contemplated. The synthesis is carried out as follows: in a first step, as already indicated above, a mixture of 11 amino acid benzyl esters (mixture A) is reacted with a corresponding mixture of 11 BOC amino acids (mixture B). After the BOC protective group is cleaved off, a reaction is carried out again, in a second step, with the same mixture of 11 BOC amino acids (mixture B). After the BOC protective groups are cleaved off of the tripeptide combinations (tripeptide library) created by the steps described above, the product is again reacted with a mixture of the 11 amino acids which have an amino functional group protected by the benzyloxycarbonyl (Z) group. The Z protective group is cleaved off at the end by means of hydrating with hydrogen. Following the building of the tetrapeptide library, and cleaving off of all protective groups, the intermediate product is lyophilized. To the unprotected tetrapeptide library so obtained a mixture of natural amino acids is preferably added, for the purpose of stabilizing and of increasing the functionality and/or specificity, with the ratio of 100 g+/−25 g peptides:80 g+/−20 g amino acid mixture. For this purpose, the library—that is, the tetrapeptide combinations—are dissolved in water and optionally spiked with a solution of the amino acids H-Asp-OH 2.41 mol-%; H-Thr-OH 9.26 mol-%; H-Ser-OH 8.61 mol-%; H-Glu-OH 6.44 mol-%; H-Pro-OH 2.30 mol-%; H-Gly-OH 4.94 mol-%; H-Ala-OH 11.69 mol-%, H-Cys-OH HCl 0.47 mol-%; H-Val-OH 6.76 mol-%; H-Met-OH 3.24 mol-%; H-Ile-OH 4.25 mol-%; H-Leu-OH 14.15 mol-%; H-Tyr-OH 0.36 mol-%; H-Phe-OH 4.27 mol-%; H-His-OH Hcl $H_2O$ 1.22 mol-%; H-Lys-OH Hcl 10.36 mol-%; and H-Arg-OI-1 HCP 9.28 mol-%, and finally lyophilized. Of course, depending on the use of the combination of peptides in a preparation, another mixture can also be contemplated other than the mixture of added amino acids named above, wherein said other mixture can have any specified mole ratio.

The problem of providing a method for the synthesis of combinations of peptides, by means of which the peptide combinations can be produced in a reproducible manner with respect to the quality and quantity thereof, is addressed by the features of claim 8.

According to the invention, a method for the synthesis of combinations of peptides is characterized in that peptides with equal sequence lengths (SEQL) are synthesized from a mixture (A) which contains:
  a number x of amino acids having a protected acid group, or a number z of peptides having acid groups protected by means of protecting groups and having activated amino groups, wherein the amino acids are present in the mixture (A) in certain, adjustable mole ratios,
and a mixture (B), containing
  a number y of amino acids having amino groups protected by means of protective groups, wherein the amino acid mole ratios in the mixture (B) are equal to the amino acid mole ratios in the mixture (A), and wherein the number x=y.

The method according to the invention preferably serves the purpose of synthesizing peptide combinations according to one of the claims 1 to 6 and/or of compiling a peptide library according to claim 14, such that the reader is directed to the description of advantages of the peptide combination according to the invention given in the earlier section of the description, and to the following description of the peptide library, for the purpose of avoiding repetition.

However, in a preferred embodiment of the method according to the invention, the reader is once more made expressly aware of the preferable addition of a mixture of natural amino acids in aqueous solution, wherein the side chain functional groups are activated by means of cleaving of the protective groups in a prior step following the synthesis of the peptides, and in a further prior intermediate step prior to spiking of the synthesized peptides with a mixture of natural amino acids in aqueous solution, the synthesized peptides are lyophilized, and are lyophilized once again following spiking with the mixture of natural amino acids, in order to obtain a powder.

The problem mentioned above of providing a peptide library, wherein the library contains combinations of peptides having the same sequence length and a certain, adjusted proportion of amino acids, is addressed by a peptide library having the features of claim 14, which claims a peptide library containing combinations of peptides each having the same sequence length of SEQL≥2, consisting of a combination of 2*11, 2*12, 2*13, 2*14, 2*15, 2*16, 2*17, or 2*18 amino acids for SEQL=2, and/or consisting of a combination of (SEQL=2)*11 to ∞, *12 to ∞, *13 to ∞, *14 to ∞, *15 to ∞, *16 to ∞, *17 to ∞, or *18 to ∞ amino acids for SEQL>2, which are present in a certain, adjustable mole ratio, wherein ∞ stands for, by way of example, ((SEQL=2)*11)*11, (((SEQL=2)*11)*11)*11, etc.

For the purpose of avoiding repetition, the reader is directed to the description of advantages of the peptide combination according to the invention and/or of the synthesis method according to the invention, with respect to the peptide library.

The present invention is explained in greater detail below with reference to the figures which are shown and discussed, and with reference to the example. It should be noted that the figures and the example are only of a descriptive nature, and are not intended to limit the invention in any way.

Example

1. Synthesis of Tetrapeptides/Tetrapeptide Library 1.1. Reagents, Solvents, and Additional Chemicals
hydroxybenzotriazole monohydrate (HOBt*H$_2$O); o-(1H-benzotriazole-1-yl)-1 1,3,3-tetramethyluronium tetrafluoroborate (TBTU); N,N-diisopropylethylamine (DIPEA); ethylacetate (EtOAc); N,N-dimethylformamide (DMF); toluene; trifluoro acetic acid (TFA); glacial acetic acid (AcOH); palladium (Pd), 10% ad carbon, with 50% water; distilled water, and sodium bicarbonate (NaHC03).

2. Synthesis Step 1: Boc-AA-OH+H-AA-OBzl.TOS or .HCl→Boc-AA-AA-OBzl 2.1 Starting Materials
Mixture B
Boc-Ala-OH, Boc-Arg(NO$_2$)—OH, Boc-Asp(OBzl)-OH, Boc-Glu(OBzl)-OH, Boc-Gly-OH, Boc-Ile-OH.½H$_2$O, Boc-LeuOH.H$_2$O, Boc-Lys(Z)—OH, Boc-Phe-OH, Boc-Pro-OH, Boc-Val-OH
Mixture A
H-Ala-OBzl.TOS, H-Arg(NO$_2$)-OBzl.TOS, H-Asp(OBzl)-OBzl.TOS, H-Glu(OBzl)-OBzl TOS H-Gly-OBzl.TOS, H-Ile-OBzl.TOS, H-Leu-OBzl.TOS, H-Lys(Z)-OBzl.HCl, Phe-OBzl.HCl, H-Pro-OBzl.HCl, H-Val-OBzl.TOS.

2.2. Synthesis Method
A reactor vessel, by way of example a 250 l vessel coated with glass, is placed under vacuum to 0.6 to 0.9 mbar, cleaned with nitrogen, and loaded with DMF (18.4 kg). Next, the following starting materials are added: Boc-Asp (OBzl)OH (553.771 g), Boc-Glu (OBzl)-OH (661.065 g), Boc-Pro-OH (671,664 g), Boc-Gly-OH (1335.986 g), Boc-Ala-OH (455.612 g), Boc-Val-OH (258.295 g), Boc-He—OH.½H$_2$O (152.469 g), Boc-Lys(Z)—OH (376.679 g), Boc-Arg(NO$_2$)—OH (235.826 g), Boc-Leu-OH.H$_2$O (7.789 g), Boc-Phe-OH (38.337 g).

A second vessel, for example a 250 l vessel coated with glass, is placed under vacuum to 0.6 to 0.9 mbar, cleaned with nitrogen, and loaded with DMF (19.4 kg). The following amino acid benzyl ester tosylates and/or hydrochlorides are added:
H-Asp (OBzl)-OBzl.TOS (831.556 g), H-Glu (OBzl)-OBzl.TOS (978.910 g), H-Pro-OBzl.HCl (754.260 g), H-Gly-OBzl.TOS (2573.058 g), H-Ala-OBzl.TOS (846.208 g), H-Val-OBzl TOS (451.143 g), H-Ile-OBzl TOS (249.683 g), H-Lys (Z) OBzl.HCl (402.887 g), H-Arg (NO$_2$)-OBzl 2 TOS (483.12 g), H-Leu-OBzl.TOS (12.294 g), H-Phe-OBzl.HCl (42.162 g).

The contents of the first reactor are introduced in their entirety into the second reactor. Along with low-level nitrogen ventilation, HOBt monohydrate (3.78 kg) is added at 20-25° C., and the mixture is stirred at 4-6° C. until complete solution is reached. TBTU (7.92 kg) is added to this solution, creating a suspension. DIPEA (9.996 kg) is added to the solution while the temperature is maintained below 15° C. The temperature is then increased to 25° C., and the mixture is stirred approximately 15 to 20 hours. Next, the DMF is entirely removed by azeotropic distillation with toluene (2×14 kg), and then the toluene is removed with EtOAc (2×9.3 kg). After another addition of EtOAc (28 kg), the reaction mixture is extracted with an 8% NaHCO$_3$ solution (51 l), then with water (30 kg), and then concentrated under vacuum to obtain an oily residue, which is used in the subsequent synthesis step 2.

3. Synthesis Step 2:
Boc-AA-AA-OBzl-H-AA-AA-OBzl.TFA 3.1 Starting Materials
The oily residue from synthesis step 1 and TFA
3.2 Synthesis Method
A reaction vessel, for example a 250 l vessel coated with glass, containing the oily residue from the prior step, is placed under vacuum to 0.6 to 0.9 mbar, cleaned with nitrogen, and loaded with trifluoroacetic acid (TFA, 30.4 kg) within 10-30 minutes. The temperature is maintained below 30° C. Concentration at 45° C. leads to an oily residue to which toluene is added (32.8 kg) to remove the residual TFA by means of azeotropic distillation. In order to ensure the complete removal of the TFA, successive doses of EtOAc (9.8 kg) and distilled water (10.3 kg) are added. Next, the reaction mixture is concentrated to an oil, and stored under vacuum at 35° C. The oil is used in the subsequent synthesis step.

4. Synthesis Step 3:
Boc-AA-OH+H-AA-AA-OBzl.TFA-Boc-AA-AA-AA-OBzl 4.1 Starting Materials
The oily residue from synthesis step 2, and Boc-Ala-OH Boc-Arg(NO$_2$)—OH Boc-Asp(OBzl)-OH Boc-Glu(OBzl)-OH, Boc-Gly-OH, Boc-Ile-OH.½H$_2$O, Boc-Leu-OH.H$_2$O, Boc-Lys(Z)—OH, Boc-Phe-OH, Boc-Pro-OH, Boc-Val-OH.

4.2 Synthesis Method
A reactor vessel, for example a 250 l vessel coated with glass, is placed under vacuum to 0.6 to 0.9 mbar, cleaned with nitrogen, and loaded with DMF (17.4). The following products are added at room temperature:
Boc-Asp(OBzl)-OH (553.771 g), Boc-Glu(OBzl)-OH (661.065 g), Boc-Pro-OH (671.664 g), Boc-Gly-OH (1335.986 g), Boc-Ala-OH (455.612 g), Boc-Val-OH (258.295 g), Boc-Ile-OH ½H$_2$O (152.469 g), Boc-Lys(Z)—OH (376.679 g), Boc-Arg (NO$_2$)—OH (235.826 g), Boc-Leu-OH.H$_2$O (7.789 g), Boc-Phe-OH (38.337 g).

A second vessel coated with glass, containing the oily residue from the prior step, is placed under vacuum and cleaned with nitrogen. Next, DMF (17.4 kg) is added, and the mixture is stirred until a homogeneous solution is obtained. The contents of the first reactor are entirely transferred to the second reactor, and HOBt monohydrate (3.78 kg) is added, and the entire mixture is stirred until all components are fully dissolved. At this point (complete solution), the solution is cooled down to 5° C., and HBTU (7.92 kg) is added, followed by the addition of DIPEA (9.996 kg), while the temperature is maintained below 10° C. This solution is concentrated at approx. 55° C. under vacuum until an oily residue is obtained. The latter is subjected to azeotropic distillation resulting from the addition of toluene, EtOAc, and water, and then further concentrated by means of vacuum. EtOAc is added to the obtained oily residue, and the organic solution is extracted multiple times with 8% sodium bicarbonate solution (NaHCO$_3$), followed by water, and then evaporated to give an oily residue. The latter is used in the next step.

5. Synthesis Step 4: Boc-AA-AA-AA-OBzl-H-AA-AA-AA-OBzl.TFA 5.1 Starting Materials
The oily residue from synthesis step 3, and TFA.
5.2 Synthesis Method
A reactor vessel, for example a 250 l vessel coated with glass, containing the oily residue from the previous step, is placed under vacuum to 0.6 to 0.9 mbar, cleaned with nitrogen, and loaded with trifluoroacetic acid (TFA 30.4 kg) within 10-30 min., at a temperature of approx. 25-30° C. An oily residue is obtained by evaporation at 45° C., toluene (32.8 kg) is added to the same, and the mixture is concentrated. In order to ensure the complete removal of the TFA, successive doses of EtOAc (9.8 kg) and distilled water (10.3 kg) are added. Next, the reaction mixture is concentrated to an oil, and stored under vacuum at 35° C. This mixture is used in the subsequent synthesis step 5.

6. Synthesis Step 5: Z-AA-OH H-AA-AA-AA-OBzl.TFA-Z-AA-AA-AA-AA-OBzl 6.1 Starting Materials
Z-Ala-OH, Z-Arg (NO$_2$)—OH, Z-Asp (OBzl)-OH, Z-Glu (OBzl)-OH, Z-Gly-OH, Z-Ile-OH, Z-Leu-OH, Z-Lys (Z)—OH, Z-Phe-OH, 1-Pro-OH, Z-Val-OH, and the oily residue from synthesis step 4; H-AA-AA-AA-OBzl.TFA.
6.2 Synthesis Method
A reactor vessel, for example a 250 l vessel coated with glass, is loaded with DMF (17.4 kg) in a nitrogen atmosphere, and stirred at room temperature. N$_\alpha$-carboxybenzyl-protected amino acids (1-AA-OH) are added as follows:
Z-Asp (OBzl)-OH (612.017 g), Z-Glu (OBzl)-OH (727, 726 g), Z-Pro-OH (777,819 g), Z-Gly-OH (1595.434 g), Z-Ala-OH (537.531 g), Z-Val-OH (298.741 g), Z-Ile-OH (168.344 g), Z-Lys (Z) OH (410.362 g), Z-Arg (NO$_2$)—OH (260.943 g), Z-Leu-OH (8.289 g) and Z-Phe-OH (43.253 g).
A second vessel, for example a 250 l vessel coated with glass, is placed under vacuum to 0.6 to 0.9 mbar and cleaned with nitrogen. This vessel is loaded with the oily residue from step 4, particularly H-AA-AA-AA OBzl.TFA and DMF (19.4 kg), and the mixture is stirred until a homogeneous solution is obtained. The contents of the first vessel (reactor) are entirely transferred to the second reactor.
HOBt monohydrate (3.78 kg) is added at room temperature, and the mixture until all of the HOBt monohydrate is dissolved [sic]. TBTU (7.92 kg) and DIPEA (9.996 kg) are slowly added under low-level nitrogen ventilation (60-90 min) at a temperature of approximately 4-6° C., and the pH value is measured again to ensure that the same falls within the range of 6.5 to 7.0 pH.

Concentration of this solution at approx. 55° C. under vacuum produces an oily residue, which is subjected to azeotropic distillation by means of the addition of, and concentration, following each step, with the following solvents: toluene, EtOAc/water. EtOAC is added to the oily residue which is obtained by evaporation of the last solution, and the solution is extracted multiple times with 8% sodium bicarbonate solution (NaHCO$_3$) and water. The combined organic phase is concentrated to an oil which is used in the following step 6.

7. Synthesis Step 6: Z-AA-AA-AA-AA-OBzl H-AA-AA-AA-AA-OH 7.1 Starting Materials
Residue oil from step 5: Z-AA-AA-AA-AA-OBzl.
7.2 Synthesis Method
AcOH (86.3 kg) is added to the oily residue from the previous step 5, and the mixture is stirred at approx. 25° C. until complete solution is achieved. The solution is subsequently hydrated.
For this purpose, a hydrating reactor (for example, 630 l) is loaded with a Pd catalyst (10% ad C, 50% H$_2$O), and inactivated by means of melting. The tetrapeptide library Z-AA-AA-AA-AA-OBzl is transferred in its entirety into the reactor containing the Pd catalyst. Hydrogen gas is introduced into the reactor, and the hydration proceeds at a maximum temperature of 40° C. and at 2500 to 3000 mbar (absolute pressure).
Upon completion of the reaction, the reaction mixture is purified by filtration, and the pure filtrate is evaporated to give an oil which is then processed by the successive addition of large amounts of EtOAc, and evaporated. The oil so obtained is dissolved in water, and the solution (approx. 8-12%) is lyophilized in the next step 7.

8. Synthesis Step 7: Lyophilization of the Tetrapeptides H-AA-AA-AA-AA-OH 8.1 Starting Materials
aqueous solution from step 6: H-AA-AA-AA-AA-OH in H$_2$O.
8.2 Synthesis Method
The lyophilization is carried out as follows:
sublimation: the solution is cooled to −40° C. within 3 hours. Next, the temperature is increased from −40° C. to 50° C. under a vacuum of 200 µbar within 48 hours;
desorption: the temperature is maintained at 50° C., and the pressure below 20 µbar over 24 hours.

9. Synthesis Step 8: H-AA-AA-AA-AA-OH+H-AA-OH→H-AA-AA-AA-AA-OH, H-AA-OH 9.1 Starting Materials
H-Asp-OH, H-Thr-OH, H-Ser-OH, H-Glu-OH, H-Pro-OH, H-Gly-OH, H-Ala-OH, H-Cys.HCl, H-Val-OH, H-Met-OH, H-Ile-OH, H-Leu-OH, H-Tyr-OH, H-Phe-OH, H-His-OH.H$_2$O.HCl, HLys-OH.HCl, H-Arg-OH.HCl.
9.2 Synthesis Method
The lyophilized tetrapeptide (A g) from the previous step, and the following L-amino acids, are added to a vessel (for example, 250 l) which is coated with glass, which is cleaned with nitrogen, and which is loaded with water: H-Asp-OH (1.559 g×(f)), H-Thr-OH (5.364 g×(f)), H-Ser-OH (4.402 g×(f)), H-Glu-OH (4.610 g×(f)), H-Pro-OH (1.285 g×(f)), H-Gly-OH (1.803 g×(f)), H-Ala-OH (5.066 g×(f)), HCys.HCl (0361 g×(f)), H-Val-OH (3.848 g×(f)), H-Met-OH (2.348 g×(f)), H-Ile-OH (2.711 g×(f)), H-Leu-OH (9.028 g×(f)), H-Tyr-OH (0.317 g×(f)), H-Phe-OH (3.429 g×(f)), H-His-OH, H$_2$O.HCl (1.242 g×(f)), H-Lys-OH.HCl (9.210 g×(f)), H-Arg-OH. HCl (9.512 g×(f)), where (f)=A g lyophilized tetrapeptide library$_{found}$/g peptide library$_{norm\ batch}$.

The obtained solution is then stirred at a temperature of approx. 40° C. until complete solution is achieved. Next, the temperature is lowered to 20-25° C. and the solution is stirred over night. Finally, the peptide solution is filtered to obtain a pure filtrate, which is lyophilized in the following step 9.

10. Synthesis Step 9: Lyophilization of GKL02; Pharmaceutical Substance 10.1 Starting Materials The filtrate from step 8

10.2 Synthesis Method

The lyophilization is carried out as follows:

sublimation: the solution is cooled to −40° C. within 3 hours. Next, the temperature is increased from −40° C. to 50° C. under a vacuum of 200 µbar within 48 hours; desorption: the temperature is maintained at 50° C., and the pressure below 20 µbar over 24 hours.

The substance obtained from step 9, which can be used as a medically effective preparation, can be subsequently packaged in powder form, as pressed tablets, filled into capsules, or in any other generic form, and stored at a temperature below 15° C.

BRIEF DESCRIPTION OF THE DRAWINGS

The following figures are included:

FIG. 1 shows a flow chart of a synthesis method for a tetrapeptide library according to the invention, and/or for tetrapeptides according to the invention. To avoid repetition, the flow diagram is hereby explained by way of reference to the description of example 1 given above.

FIG. 2 shows chromatograms of batches of GKL-02 prepared in series: batch 1=GKL02 SC02808L1; batch 2=GKL02 15935-AA/2, and batch 3=GKL02 15507-AA/9. Using internal standards (see arrow), identical patterns of the subsequent, identical peaks can be detected for all three batches, providing an indication of excellent consistency—that is, of reproducibility of the peptide libraries produced by means of the method according to the invention. Particularly, the chromatograms shown are evidence for the consistent reproducible quality and quantity of the peptide combinations according to the invention.

Figure 1:
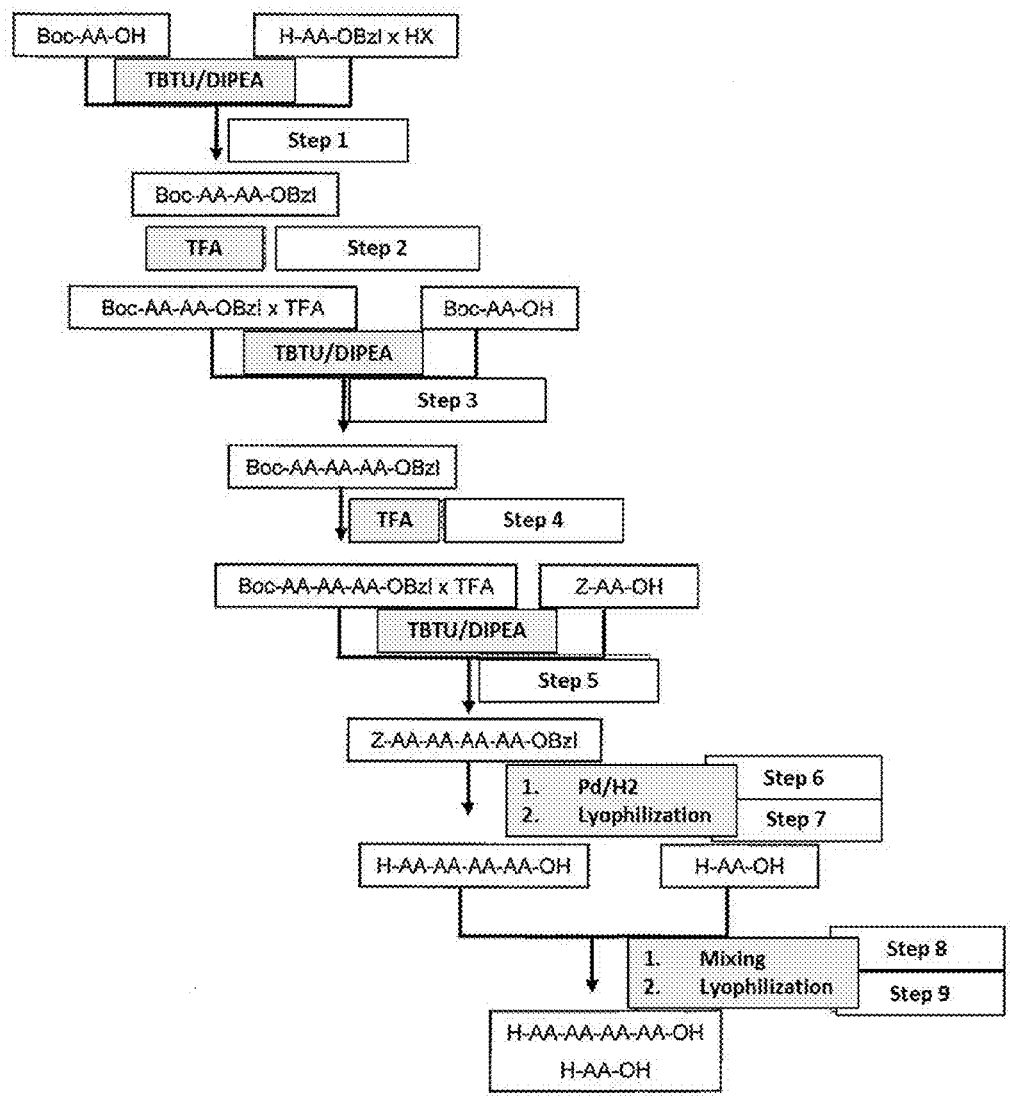
FIG. 1 a flow chart of the synthesis method described in example 1.
Figure 2:
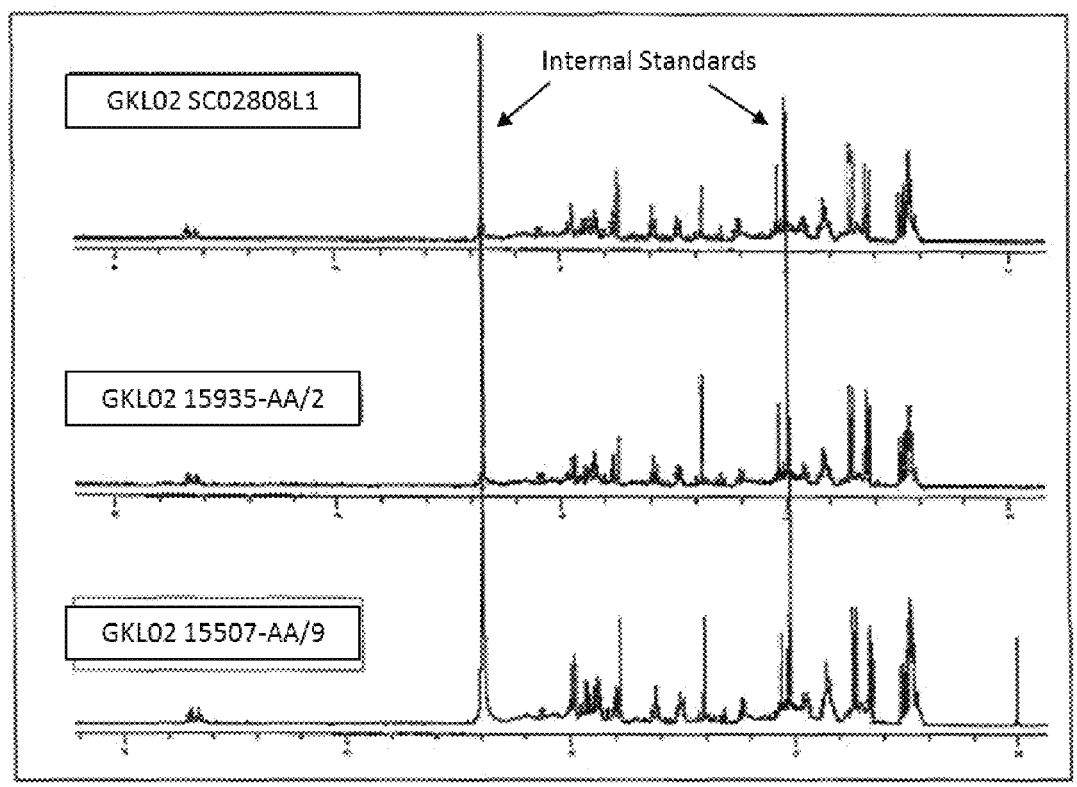
FIG. 2 a chromatogram of sequential batches of GKL-02, with internal standard.

That which is claimed:

1. A combination of peptides comprising tetrapeptides, wherein the amino acids of said combination of peptides consist of a number x of different amino acids, wherein x is selected from 11 up to and including 18, and wherein said combination is produced by:
   a) combining:
      i) a first mixture (A) comprising said number x of different amino acids having a protected acid group, and wherein the amino acids comprising at least aspartate, glutamate, proline, and glycine, wherein the amino acids are present in the first mixture (A) in certain, adjustable mole ratios, and wherein aspartate is present in 8.33 mol-%, glutamate is present in 9.53 mol-%, proline is present in 15.18 mol-%, and glycine is present in 37.10 mol-%; and,
      ii) a first mixture (B) comprising said number x of amino acids having amino groups protected by means of protective groups, wherein the amino acid mole ratios in the first mixture (B) are equal to the amino acid mole ratios in the first mixture (A);
   b) activating the protected amino functional groups of the resulting combination of peptides comprising dipeptides by cleavage of the amino protective groups, thereby producing a combination of peptides comprising dipeptides having protected acid groups and having activated amino groups;
   c) combining:
      i) a second mixture (A) comprising said combination of peptides comprising dipeptides having protected acid groups and having activated amino groups; and,
      ii) a second mixture (B) comprising said number x of amino acids having amino groups protected by means of protective groups, wherein the amino acid mole ratios in the second mixture (B) are equal to the amino acid mole ratios in the second mixture (A);
   d) activating the protected amino functional groups of the resulting combination of peptides comprising tripeptides by cleavage of the amino protective groups, thereby producing a combination of peptides comprising tripeptides having protected acid groups and having activated amino groups;
   e) combining:
      i) a third mixture (A) comprising said combination of peptides comprising tripeptides having protected acid groups and having activated amino groups; and,
      ii) a third mixture (B) comprising said number x of amino acids having amino groups protected by means of protective groups, wherein the amino acid mole ratios in the third mixture (B) are equal to the amino acid mole ratios in the third mixture (A).

2. The combination of peptides of claim 1, wherein the side chain functional groups of the amino acids are protected by means of protective groups.

3. The combination of peptides of claim 1, wherein the combination of peptides is spiked with a mixture of natural amino acids in a ratio of 100 g+/−25 g tetrapeptides:80 g+/−20 g amino acid mixture.

4. A preparation comprising the combination of peptides of claim 1, wherein said preparation is oncologically, immunologically, dermatologically, and/or endocrinologically effective.

5. A method for synthesizing a combination of peptides comprising tetrapeptides, wherein the amino acids of said combination of peptides consist of a number x of different amino acids, wherein x is selected from 11 up to and including 18, said method comprising:
   a) combining:
      i) a first mixture (A) comprising said number x of different amino acids having a protected acid group, and wherein the amino acids comprising at least aspartate, glutamate, proline, and glycine, wherein the amino acids are present in the first mixture (A) in certain, adjustable mole ratios, and wherein aspartate is present in 8.33 mol-%, glutamate is present in 9.53 mol-%, proline is present in 15.18 mol-%, and glycine is present in 37.10 mol-%; and,
      ii) a first mixture (B) comprising said number x of amino acids having amino groups protected by means of protective groups, wherein the amino acid mole ratios in the first mixture (B) are equal to the amino acid mole ratios in the first mixture (A);
   b) activating the protected amino functional groups of the resulting combination of peptides comprising dipeptides by cleavage of the amino protective groups, thereby producing a combination of peptides comprising dipeptides having protected acid groups and having activated amino groups;
   c) combining:
      i) a second mixture (A) comprising said combination of peptides comprising dipeptides having protected acid groups and having activated amino groups; and,
      ii) a second mixture (B) comprising said number x of amino acids having amino groups protected by means of protective groups, wherein the amino acid mole ratios in the second mixture (B) are equal to the amino acid mole ratios in the second mixture (A);
   d) activating the protected amino functional groups of the resulting combination of peptides comprising tripeptides by cleavage of the amino protective groups, thereby producing a combination of peptides comprising tripeptides having protected acid groups and having activated amino groups;
   e) combining:
      i) a third mixture (A) comprising said combination of peptides comprising tripeptides having protected acid groups and having activated amino groups; and,
      ii) a third mixture (B) comprising said number x of amino acids having amino groups protected by means of protective groups, wherein the amino acid mole ratios in the third mixture (B) are equal to the amino acid mole ratios in the third mixture (A).

6. The method of claim 5, wherein the side chain functional groups of the amino acids are protected by means of protective groups.

7. The method of claim 6, wherein following the synthesis of the combination of peptides comprising tetrapeptides, the protected acid-, amino-, and side chain functional groups are activated by cleavage of the protecting groups, and in an intermediate step, the peptides are lyophilized and are mixed with a mixture of natural amino acids in aqueous solution, wherein the ratio of the peptides to the amino acid mixture is 100 g+/−25 g peptides: 80 g+/−20 g amino acid mixture, and/or the peptide-amino acid mixture is lyophilized in a following step.

* * * * *